United States Patent [19]

Morgan

[11] Patent Number: 4,810,814

[45] Date of Patent: Mar. 7, 1989

[54] PREPARATION OF CYANOALKYLPHENOLS

[75] Inventor: Ted A. Morgan, Midland, Mich.

[73] Assignee: The Dow Chemical Company, Midland, Mich.

[21] Appl. No.: 911,848

[22] Filed: Sep. 26, 1986

[51] Int. Cl.$^4$ .......................................... C07C 120/02
[52] U.S. Cl. .................................... 558/335
[58] Field of Search ......................... 558/335

[56] References Cited

U.S. PATENT DOCUMENTS

| | | | |
|---|---|---|---|
| 2,803,640 | 8/1957 | Heckert et al. | 558/335 |
| 3,064,034 | 11/1962 | Kreysa | 558/335 |
| 4,388,250 | 6/1983 | Farber et al. | 564/389 |
| 4,405,528 | 9/1983 | Everly | 562/478 |
| 4,483,800 | 11/1984 | Everly et al. | 562/478 |
| 4,485,051 | 11/1984 | Everly et al. | 562/478 |
| 4,487,722 | 12/1984 | Everly et al. | 562/478 |

FOREIGN PATENT DOCUMENTS 0096640 6/1983 European Pat. Off. .

OTHER PUBLICATIONS

I. O. Sutherland, "Nitrogen Compounds, Carboxylic Acids, Phosphorus Compounds", vol. 2 of the series *Comprehensive Organic Chemistry,* ed. Sir D. Barton, F.R.S., W. D. Ollis, F.R.S., Pergamon Press, New York, 1978.

A. Johnsson, *Acta. Chem. Scand.,* 8, 1203–10 (1954).

*Primary Examiner*—Anton H. Sutto

[57] ABSTRACT

A method for preparing cyanaolkylphenols such as 4-(1-cyano-1-methylethyl)phenol by reacting cyanide ion in a form such as sodium cyanide with an alkenyl phenol such as 4-(2-propenyl)phenol.

The cyanoalkylphenols are useful as chemical intermediates in the preparation of polyurethanes, polycarbonate monomers and epoxy resins.

18 Claims, No Drawings

PREPARATION OF CYANOALKYLPHENOLS

BACKGROUND OF THE INVENTION

This invention relates to the preparation of cyanoalkylphenols. More specifically, this invention pertains to a process for reacting cyanide ion with p-alkenylphenols to produce the corresponding cyanoalkylphenols.

The cyanoalkylphenols produced by the process of the present invention have numerous applications and are particularly useful as chemical intermediates in the preparation of polyurethane epoxy resins and pharmaceutical and agricultural products.

The preparation of certain cyanoalkyl compounds can be accomplished by the addition of hydrogen cyanide or cyanide ion to multiple bonds (hydrocyanation). Although simple alkenes are inert towards hydrocyanation, the reaction is promoted by both electron-donating and electron-withdrawing substituents. See I. O. Sutherland, "Nitrogen Compounds, Carboxylic Acids, Phosphorus Compounds", Vol. 2 of the series *Comprehensive Organic Chemistry*, ed. Sir D. Barton, F.R.S., W. D. Ollis, F.R.S., Pergamon Press, New York, 1978. Heretofore, the direct hydrocyanation of alkenylphenols has not been accomplished due to inertness, oligomerization, or other side reactions.

A process for the preparation of cyanoalkylphenols involves a complex multi-step synthesis whereby a dimethylbenzylhalide is converted to the cyanide, ring nitrated, hydrogenated, and then subjected to diazotization. See A. Johnsson, *Acta. Chem. Scand.*, 8, 1203–10 (1954). The problem with this process is that it is a low-yielding, multi-step, time-consuming, and uneconomical route.

A process for the preparation of cyanoalkylphenols is needed that would avoid hydrolysis, isomer formation, and oligomerization.

SUMMARY OF THE INVENTION

The present invention is a process for the preparation of cyanoalkylphenols which avoids many of the problems associated with prior methods. The process of the present invention comprises contacting an alkenyl phenol with cyanide ion under reaction conditions sufficient to produce a cyanoalkylphenol.

It has been discovered that carrying the reaction out in the presence of a proton source such as phenol allows the direct reaction of cyanide ion with an alkenyl phenol to proceed beyond 50 percent conversion to cyanoalkylphenol. The problems of oligomerization and reversibility are substantially eliminated under the reaction conditions of the present invention.

DETAILED DESCRIPTION OF THE INVENTION

The preferred alkenyl phenols useful in the process of the present invention correspond to the following general formula:

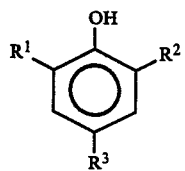

wherein $R^1$, $R^2$ and $R^3$ are independently hydrogen, $C_{2-10}$ alkenyl, more preferably $C_{3-10}$ alkenyl, $C_{3-10}$ cycloalkenyl, $C_{1-20}$ alkyl, $C_{3-10}$ cycloalkyl, arylalkyl or alkylaryl, with the proviso that at least one of $R^1$, $R^2$ and $R^3$ must be an alkenyl group with the double bond of said alkenyl group being in conjugation with the aromatic ring of the phenol. Conjugation herein refers to the double bond of the alkenyl group being removed from the aromatic ring of the phenol by one single bond and is illustrated by the following formula:

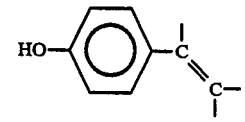

as well as unsaturated groups wherein the double bond can migrate under the conditions of the reaction into conjugation with the aromatic ring.

Suitable alkenylphenols include 4-(2-propenyl)phenol, 2-(2-propenyl)phenol, 4-(2-(1-butenyl))phenol, 2-(2-(1-butenyl))phenol, 4-(2-(2-butenyl))phenol, 2-(2-(2-butenyl))phenol, 4-(2-(2-pentenyl))phenol, 2-(2-(2-pentenyl))phenol, 4-(3-(2-pentenyl))phenol, 2-(3-(2-pentenyl))phenol, 4-(2-(2-hexenyl))phenol, 2-(2-(2-hexenyl))phenol, 4-(3-(2-hexenyl))phenol, 2-(3-(2-hexenyl))phenol, 4-(2-(1-hexenyl))phenol, 2-(2-(1-hexenyl))phenol, 4-(3-(3-hexenyl))phenol, 2-(3-(3-hexenyl))phenol, 4-(1-cyclohexenyl)phenol, 2-(1-cyclohexenyl)phenol, 4-(1-cyclopentenyl)phenol, 2-(1-cyclopentenyl)phenol, 4-(1-cycloheptenyl)phenol, 2-(1-cycloheptenyl)phenol. Preferred are 4-(2-propenyl)phenol, 4-(2-(1-butenyl))phenol, 4-(2-(2-pentenyl))phenol, 4-(3-(2-pentenyl))phenol, 4-(2-(2-hexenyl))phenol, 4-(3-(2-hexenyl))phenol, 4-(2-(1-hexenyl))phenol, 4-(3-(3-hexenyl))phenol, 4-(1-cyclohexenyl)phenol, 4-(1-cyclopentenyl)phenol, and 4-(1-cycloheptenyl)phenol, 4-ethenylphenol, 2-ethenylphenol. Also suitable are 4- and 2-alkenylphenols having substituents on the aromatic ring and/or the alkenyl moiety such as halo, e.g., chloro and bromo; alkyl, e.g., methyl, ethyl, propyl and others having up to 6 carbons; aryl, e.g., phenyl; alkoxy, e.g., methoxy; nitro; amino; sulfo; cyano; carboxy; acyl and the like. Of these, 4-(2-propenyl)phenol is the most preferred. ferred.

Cyanide ion as used herein means a cyanide ion in salt form and specifically excludes hydrogen cyanide. Suitable forms of cyanide ion include lithium, tetraalkylammonium, sodium and potassium. Preferred forms of cyanide ion include sodium and potassium cyanide, with sodium cyanide being most preferred. The cyanide ion is used in an amount sufficient to hydrocyanate substantially 111 of the alkenyl phenol starting material. The molar ratio of cyanide ion to alkenyl phenol is typically in the range of from about 1.0 to about 10, with about 1.0 to about 2.0 being preferred. The most preferred molar ratio is about 1.1.

A mild acid is advantageously employed in the process of the present invention. Any mild acid that has a pKa in the range from about 8 to about 12 can be utilized. The presence of a mild acid enhances the rate to 100 percent conversion. Suitable mild acids include dimethylglycine, o-cresol, m-cresol, p-cresol, hydroxyquinoline, lysine, methylglycine, p-chlorophenol, α-naphthol, β-naphthol, phenol, pyrocatechol, resorcinol, and tryptophan. Preferred mild acids include o-cresol, m-cresol, p-cresol, α-naphthol, β-naphthol, phenol, pyrocatechol, and resorcinol with phenol being the most preferred. The mild acid is used in an amount which will ensure a substantial completion of the hydrocyanation. The molar ratio of mild acid to alkenyl phenol is suitably in the range of from about 0.1 to about 10, preferably from about 1.0 to about 2.0, with 1.1 being most preferred.

A solvent is also advantageously employed in the process of the present invention. Any solvent which is unreactive and will dissolve the starting materials can be employed in the present process. Aprotic solvents such as N,N-dimethylformamide, dioxane, dimethylformamide, dimethylsulfoxide, formamide, glyme, diglyme, glycol, hexamethylphosphoramide, or N-methylpyrrolidone are preferred with N,N-dimethylformamide being the most preferred solvent. When solvent is employed, it is used in amounts sufficient to dissolve a sufficient amount of reactants to facilitate the reaction, preferably in amounts in the range from about 50 to about 75 weight percent based on the weight of the reaction medium.

The process of the present invention can be carried out at any temperature at which the reaction will proceed. Preferably, the reaction mixture is elevated to a temperature in the range from about 80° C. to about 150° C. The process is carried out for a period of time which will allow substantial conversion of the starting material. Preferred reaction times are in the range from about 5 to about 50 hours, with the range from about 10 to about 30 hours being most preferred.

Conversions and yields typically obtained in the practice of the process of this invention are in the range from about 95 to 100 percent and from about 90 to about 95 percent, respectively.

A preferred manner of practicing the present invention involves heating a mixture of an alkenyl phenol, cyanide ion, a mild acid and an aprotic solvent to a temperature above 100° C. and maintaining the mixture at that temperature for over 20 hours. The product is removed by typical methods of distillation, extraction and filtration. The preferred embodiment of the process of the present invention can be represented by the following reaction scheme:

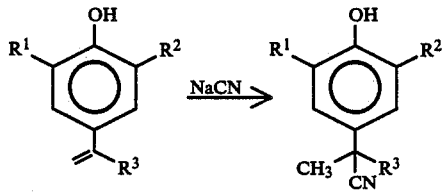

wherein $R^1$ and $R^2$ are as defined above and in this case $R^3$ is an alkyl group.

Typical cyanoalkylphenols prepared by the process of the present invention include 4-(1-cyano-1-methylethyl)phenol, 2-(1-cyano-1-methylethyl)phenol, 4-(2-(2-cyanobutyl))phenol, 2-(2-(2-cyanobutyl))phenol, 4-(2-(2-cyanopentyl))phenol, 2-(2-(2-cyanopentyl))phenol, 4-(3-(3-cyanopentyl))phenol, 2-(3-(3-cyanopentyl))phenol, 4-(2-(2-cyanohexyl))phenol, 2-(2-(2-cyanohexyl))phenol, 4-(3-(3-cyanohexyl))phenol, 2-(3-(3-cyanohexyl))phenol, 4-(1-(1-cyanocyclohexyl))phenol, 2-(1-(1-cyanocyclohexyl))phenol, 4-(1-(1-cyanocyclopentyl))phenol, 2-(1-(1-cyanocyclopentyl))phenol, 4-(1-(1-cyanocycloheptyl))phenol, and 2-(1-(1-cyanocycloheptyl))phenol, with 4-(1-cyano-1-methylethyl)phenol, 4-(2-(2-cyanobutyl))phenol, 4-(2-(2-cyanopentyl))phenol, 4-(3-(3-cyanopentyl))phenol, 4-(2-(2-cyanohexyl))phenol, 4-(3-(3-cyanohexyl))phenol, 4-(1-(1-cyanocyclohexyl))phenol, 4-(1-(1-cyanocyclopentyl))phenol, and 4-(1-(1-cyanoheptyl))phenol being preferred. The most preferred cyanoalkylphenol is 4-(1-cyano-1-methylethyl)phenol.

SPECIFIC EMBODIMENTS

The following example further illustrates the invention and should not be construed as limiting its scope. All parts and percentags are by weight unless otherwise indicated.

EXAMPLE 1

To a one-liter round-bottom flask equipped with a magnetic stir bar, reflux condenser and thermometer is added a mixture of 134 g (1.0 mole) of 4-(2-propenyl)-phenol, 103 g (1.1 moles) of phenol, 54 g (1.1 moles) of sodium cyanide and 500 ml of N,N-dimethylformamide. The mixture is heated to 100° C. and held at 100° C. for 30 hours. A substantial portion of the N,N-dimethylformamide is removed by vacuum distillation (45° C./1.0 mm Hg) to give a brown solid. The solid is acidified with aqueous hydrogen chloride and extracted with $CHCl_3$. The $CHCl_3$ layer is dried over $MgSO_4$, filtered and concentrated to give a brown liquid. The remaining N,N-dimethylformamide and phenol are removed by distillation at 65° C./1.0 mm Hg to give 190 g of a brown solid. The solid is dissolved in one liter of $CHCl_3$, filtered through silica gel and then recrystallized from 1:1 $CHCl_3$/hexane (hot) to give 145 g of a colorless crystalline solid (m.p. 99° C.–101° C.). Overall yield is 90 percent based on 4-(2-propenyl)phenol with 100 percent conversion.

What is claimed is:

1. A process comprising contacting an alkenyl phenol with cyanide ion under reaction conditions sufficient to form a cynanoalkylphenol, said alkenyl phenol corresponding to the formula:

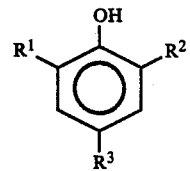

wherein $R^1$, $R^2$, and $R^3$ are independently hydrogen, $C_{2-10}$ alkenyl, $C_{3-10}$ cycloalkenyl, $C_{1-20}$ alkyl, $C_{3-10}$ cycloalkyl, arylalkyl or alkylaryl, with the proviso that at least one of $R^1$, $R^2$, and $R^3$ must be an alkenyl group with the double bond of said alkenyl group being in conjugation with the aromatic ring of the phenol.

2. The process of claim 1 wherein the alkenyl phenol is 4-(2-propenyl)phenol, 4-(2-butenyl)phenol or 4-(2-cyclohexenyl)phenol.

3. The process of claim 2 wherein the alkenyl phenol is 4-(2-propenyl)phenol.

4. The process of claim 1 wherein the cyanide ion is in the form of sodium cyanide or potassium cyanide.

5. The process of claim 3 wherein the cyanide ion is in the form of sodium cyanide.

6. A process comprising contacting an alkenyl phenol, cyanide ion, a mild acid having a pKa in the range from about 8 to about 12 and a solvent under reaction conditions sufficient to form a cyanoalkylphenol, said alkenyl phenol corresponding to the formula:

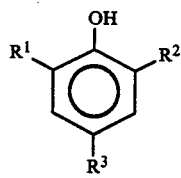

wherein $R^1$, $R^2$, and $R^3$ are independently hydrogen, $C_{2-10}$ alkenyl, $C_{3-10}$ cycloalkenyl, $C_{1-20}$ alkyl, $C_{3-10}$ cycloalkyl, arylalkyl or alkylaryl, with the proviso that at least one of $R^1$, $R^2$, and $R^3$ must be an alkenyl group with the double bond of said alkenyl group being in conjugation with the aromatic ring of the phenol.

7. The process of claim 6 wherein the alkenyl phenol is 4-(2-propenyl)phenol, 4-(2-butenyl)phenol or 4-(2-cyclohexenyl)phenol.

8. The process of claim 7 wherein the alkenyl phenol is 4-(2-propenyl)phenol.

9. The process of claim 6 wherein the cyanide ion is in the form of sodium cyanide or potassium cyanide.

10. The process of claim 8 wherein the cyanide ion is in the form of sodium cyanide.

11. The process of claim 6 wherein the mild acid is phenol, m-cresol, o-cresol, p-cresol, α-naphthol, β-naphthol, pyrocatechol, or resorcinol.

12. The process of claim 10 wherein the mild acid is phenol.

13. The process of claim 6 wherein the solvent is an aprotic solvent.

14. The process of claim 6 wherein the solvent is dioxane, dimethylformamide, glyme, diglyme, dimethylsulfoxide, formamide, hexamethylphosphoramide or N-methylpyrrolidone.

15. The process of claim 12 wherein the solvent is dimethylformamide.

16. A process for the preparation of 4-(1-cyano-1-methylethyl)phenol comprising (1) forming a mixture of 4-(2-propenyl)phenol, sodium cyanide, phenol and dimethylformamide, (2) heating the mixture to about 100° C., (3) maintaining the mixture at 100° C. for about 30 hours and (4) isolating the product by distillation and extraction.

17. A process for preparing a cyanoalkyl phenol comprising contacting an alkenyl phenol with a cyanide ion in a reaction medium containing an aprotic solvent and a mild acid at a temperature in the range from about 80° C. to about 150° C. for a time and under conditions sufficient to produce the cyanoalkyl phenol in a yield in the range from about 90 to 95 percent, said alkenyl phenol corresponding to the formula:

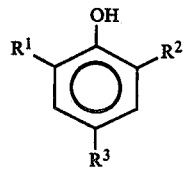

wherein $R^1$, $R^2$, and $R^3$ are independently hydrogen, $C_{2-10}$ alkenyl, $C_{3-10}$ cycloalkenyl, $C_{1-20}$ alkyl, $C_{3-10}$ cycloalkyl, arylalkyl or alkylaryl, with the proviso that at least one of $R^1$, $R^2$, and $R^3$ must be an alkenyl group with the double bond of said alkenyl group being in conjugation with the aromatic ring of the phenol.

18. The process of claim 17 wherein the cyanide ion is provided in salt form, the cyanide ion is present in a molar ratio to the alkenyl phenol in the range of from about 1:1 to about 10:1, the aprotic solvent is N,N-dimethylformamide, dioxane, dimethylformamide, dimethylsulfoxide, formamide, glyme, diglyme, gylcol, hexamethylphosphoramide or N-methylpyrrolidone and the aprotic solvent is present in an amount in the range from about 50 to about 75 weight percent based on the weight of the reaction medium, the mild acid has a pK in the range from about 8 to about 12, and the time is in the range from about 5 to about 50 hours.

* * * * *